US006448055B1

(12) United States Patent
Shimizu et al.

(10) Patent No.: US 6,448,055 B1

(45) Date of Patent: Sep. 10, 2002

(54) Δ9-DESATURASE GENE

(75) Inventors: Sakayu Shimizu; Michihiko Kobayashi, both of Kyoto (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/380,262

(22) PCT Filed: Feb. 27, 1998

(86) PCT No.: PCT/JP98/00819

§ 371 (c)(1), (2), (4) Date: Aug. 27, 1999

(87) PCT Pub. No.: WO98/38314

PCT Pub. Date: Sep. 3, 1998

(30) Foreign Application Priority Data

Feb. 27, 1997 (JP) ............................................ 9-044303

(51) Int. Cl.[7] ............................ C12N 9/02; C12N 1/14; C12N 1/20; C12P 7/64; C07H 21/04

(52) U.S. Cl. ................ 435/189; 435/254.3; 435/252.3; 435/134; 435/71.1; 536/23.2

(58) Field of Search ............................... 435/71.1, 134, 435/189, 252.3, 254.3; 536/23.2

(56) References Cited

U.S. PATENT DOCUMENTS 5,536,661 A * 7/1996 Boel et al. ............... 435/254.3

FOREIGN PATENT DOCUMENTS

EP 0 561 569 A2 9/1993

OTHER PUBLICATIONS

Meesters, P.A.E.P. et al., "Cloning and expression of the delta–9 fatty desaturase gene from *Cryptococus curvatus* ATCC 20509 containing histidine boxes and a cytochrome $b_5$ domain" Appl. Microbol. Biotechnol. (Aug. 1997), vol. 47, p. 663–667.

Patricia, A. et al., "Isolation and characterization of a delta–9 Fatty Acid Desaturase Gene from the Oleaginous Yeast *Crypt ococus curvatus* CBS 570", Yeast (1996), vol. 12, pp. 723–730.

Slivana, G. et al., "A Temperature–Sensitive Strain of *Histoplasma capsulatum* Has an Altered delta–9–Fatty Acid Desaturase Gene", Lipid (1995) vol. 30, No. 10, pp. 899–906.

Joseph, E.S. et al., "The OLE1 Gene of *Saccharomyces cervisiae* Encodes the delta–9 Fatty Acid Desaturase and Can Be functionally Replaced by the Rat Stearoyl–CoA Desaturated Gene", J. Biol. Chem. (1990), vol. 265, No. 33, pp. 20144–20149.

James, M.N. et al., "Differentiation–induced Gene Expression in 3T3–L1 Preadipocytes", J. Biol. Chem., (1988), vol. 263, No. 33, pp. 17291–17300.

(List continued on next page.)

*Primary Examiner*—Ponnathapura Achutamurthy

(74) *Attorney, Agent, or Firm*—Paul E. White, Jr.; Manelli Denison & Selter PLLC

(57) ABSTRACT

Genomic DNA and cDNA encoding Δ9-desaturase from a microorganism belonging to the subgenus Mortierella of the genus Mortierella, an expression vector for expression thereof, and a transformant are disclosed. A method for producing Δ9-desaturase by use of a gene encoding the enzyme is also disclosed. Introduction of the Δ9-desaturase gene of the present invention into an unsaturated fatty acid producing cell can enhance conversion into palmitoleic acid or oleic acid, starting materials for unsaturated fatty acids, and can increase the production of unsaturated fatty acids. By combining a gene for cytochrome b5 or a gene for cytochrome b5 reductase, constituents of the microsomal electron transport system, with the Δ9-desaturase of the present invention, more efficient production can be expected. Δ9-desaturase can also be produced with high efficiency by a recombinant DNA technology.

8 Claims, 26 Drawing Sheets

OTHER PUBLICATIONS

Shimizu S. et al., "Sesamin is a potent and Specific Inhibitor of delta–5 Desaturase in Polyunsaturated Fatty Acid Biosynthesis", Lipid (1991), vol. 26, No. 7, pp. 512–516.

Laoteng K. et al. "Cloning of a Cold–Induced Gene Encoding Stearoyl–CoA Desaturase From MUCOR ROUXII" Data Base EMBL, Nov. 5, 1997.

Meesters P.A.E.P. et al "Delta–9 Fatty Acid Desaturase Gene (Ole1) From *Cryptococcus Curvatus* ATCC 20509" Data Base EMBL. Jan. 13, 1997.

Meesters P.A.E.P. et al "Delta–9 Fatty Acid Desaturase Gene (Ole1) From *Cryptococcus Curvatus* CBS 570" Data Base EMBL. Jan. 13, 1997.

Gargano S. et al. Delta–9 Fatty Acid Desaturase Gene (Ole1) From *Histoplasma Capsulatum* (Strain G217B) Data Base EMBL. Mar. 30, 1995.

Gargano S. et al. Delta–9 Fatty Acid Desaturase Gene (Ole1) From *Histoplasma Capsulatum* (Strain Downs) Data Base EMBL. Mar. 30, 1995.

Stuky J. E. et al. "*Saccharomyces Cerevisiae* Delta–9 Fatty Acid Desaturase (Ole1) Gene" Data Base EMBL. Mar. 18, 1994.

Shimizu S. et al. "Production of Polyunsaturated Fatty Acids by Filamentous Fungi" Vitamins, vol. 66, No. 5–6, 1992, pp. 289–299.

Shimizu S. et al. "Production of Useful Fatty Acids by Microbiol Process" Recent Res. Dev. Lipids Res., vol. 1, 1997, pp. 267–286.

N. Amano et al. Mycotaxon Chemotaxonomic Significance of Fatty Acid Composition In the Genus Mortierella (Zygomycetes, Mortierellaceae) vol. XLIV No. 2, (1992) pp. 257–265.

M. Certik and S. Shimizu Recent Res. Devel. In Oil Chem. "Progress in polyunsaturated fatty acid production by fungi" No. 2 (1998) pp. 191–192.

* cited by examiner

FIG. 1A

```
        10         20         30         40         50         60
GAATTCGAGG ATCCGGGTAC CATGGCTCTT TCGCACTCTT GTTCGATAGC TCGTACCTTT

        70         80         90        100        110        120
TACTCTTCAT CCTTGGTGGA ACACTGCTGC CGAAGCAACT CCTCCTTTCA CACCCTCGAC

       130        140        150        160        170        180
CTCAAACAAC TCGCACTCCG GATCGAAGAG TGCAGCAACG CAGGACGCAC AGCGATGGCA

       190        200        210        220        230        240
ACTCCTCTCC CCCCCTCCTT CGTCGTCCCC GCGACACAGA CGGAAACCCG CAGAGATCCT

       250        260        270        280        290        300
CTCCAGCACG AGGAACTGCC CCCTCTCTTC CCCGAGAAAA TCACCATTTA CAACATCTGG

       310        320        330        340        350        360
AGATATCTTG ACTACAAGCA TGTTGTTGGT CTGGGACTGA CACCTTTGAT CGCACTCTAC

       370        380        390        400        410        420
GGCCTTTTGA CGACCGAGAT CCAGACGAAG ACCCTGATCT GGTCCATCAT CTACTACTAC

       430        440        450        460        470        480
GCTACGGGCC TTGGTATCAC AGCAGGTTAT CATCGACTCT GGGCCCATCG TGCCTACAAC
```

FIG. 1B

| 490 | 500 | 510 | 520 | 530 | 540 |
|---|---|---|---|---|---|
| GCAGGACCTG | CCATGAGCTT | CGTACTCGCA | CTGCTTGGCG | CTGGTGCTGT | TGAAGGATCT |
| **550** | **560** | **570** | **580** | **590** | **600** |
| ATCAAGTGGT | GGTCCCGCGG | CCACCGTGCT | CACCACCGTT | GGACAGACAC | CGAGAAGGAT |
| **610** | **620** | **630** | **640** | **650** | **660** |
| CCCTATAGCG | CTCACCGCGG | ACTTTTTTTC | TCGCACATTG | GCTGGATGCT | GATCAAGCGT |
| **670** | **680** | **690** | **700** | **710** | **720** |
| CCTGGATGGA | AGATTGGCCA | TGCCGATGTC | GACGACCTCA | ACAAGAGCAA | ACTCGTTCAG |
| **730** | **740** | **750** | **760** | **770** | **780** |
| TGGCAGCACA | AGAACTACCT | CCCTCTTGTT | CTTATTATGG | GTGTTGTCTT | CCCCACACTT |
| **790** | **800** | **810** | **820** | **830** | **840** |
| GTTGCTGGTC | TCGGCTGGGG | CGACTGGCGC | GGAGGTTACT | TCTATGCTGC | CATTCTTCGT |
| **850** | **860** | **870** | **880** | **890** | **900** |
| CTTGTCTTTG | TCCACCACGC | CACCTTTTGT | GTCAACTCCC | TGGCTCACTG | GCTCGGCGAT |
| **910** | **920** | **930** | **940** | **950** | **960** |
| GGACCCTTTG | ATGACCGCCA | CTCCCCCCGC | GACCACTTTA | TCACTGCCTT | TGTCACTTTG |

FIG. 1C

```
       970        980        990       1000       1010       1020
GGCGAAGGTT ACCACAACTT CCATCACCAG TTCCCCCAGG ACTACCGCAA CGCTATCCGT

      1030       1040       1050       1060       1070       1080
TTCTACCAGT ACGACCCTAC AAAGTGGGTC ATTGCCCTCT GCGCTTTCTT TGGCCTCGCT

      1090       1100       1110       1120       1130       1140
TCTCACCTCA AGACCTTCCC TGAGAATGAA GTTCGCAAGG GTCAGCTCCA GATGATTGAG

      1150       1160       1170       1180       1190       1200
AAGCGTGTCT TGGAGAAGAA GACCAAGCTT CAGTGGGGCA CCCCCATTGC CGATCTGCCC

      1210       1220       1230       1240       1250       1260
ATTCTGAGCT TTGAGGACTA CCAGCATGCC TGCAAGAACG ACAACAAGAA GTGGATTCTA

      1270       1280       1290       1300       1310       1320
TTGGAGGGCG TCGTCTACGA TGTTGCTGAC TTCATGTCAG AGCACCCTGG AGGTGAGAAG

      1330       1340       1350       1360       1370       1380
TACATCAAGA TGGGCGTTGG CAAGGACATG ACTGCAGCCT TCAACGGCGG CATGTACGAT
```

FIG. 2

```
      1390       1400       1410       1420       1430       1440
CACAGCAACG CCGCCCGCAA CTTGCTGAGC TTGATGCGCG TTGCCGTCGT TGAGTATGGT

      1450       1460       1470       1480       1490       1500
GGTGAAGTTG AGGCTCAGAA GAAGAACCCT TCGATGCCCA TCTACGGCAC TGACCACGCC

      1510       1520       1530       1540       1550       1560
AAGGCCGAAT AGACGGCGAG CTGGCCTGGC CCCTTGTGCG CATTACACCA CTATACCTCC

      1570       1580       1590       1600       1610       1620
ACCCTCTCTT TTGAGTATTC TTTGTTAGTC CTACATTTCA CATCGACTCC CTTGCAGCTA

      1630       1640       1650       1660       1670       1680
TTCATGAACA CATAGCTCAC TCCTTGTACC ATTTCCAACC TCCCTGCATC CTGTAATAAA

      1690       1700       1710       1720       1730       1740
CACTCGTTCT ACAACCGAAA AAAAAAAAAA AAAAAAAAAC CATGGTACCC GGATCCTCGA

      1750       1760       1770       1780       1790       1800
ATTC
```

FIG. 3

```
        10         20         30         40         50         60
MATPLPPSFV VPATQTETRR DPLQHEELPP LFPEKITIYN IWRYLDYKHV VGLGLTPLIA

        70         80         90        100        110        120
LYGLLTTEIQ TKTLIWSIIY YYATGLGITA GYHRLWAHRA YNAGPAMSFV LALLGAGAVE

       130        140        150        160        170        180
GSIKWWSRGH RAHHRWTDTE KDPYSAHRGL FSHIGWMLI KRPGWKIGHA DVDDLNKSKL

       190        200        210        220        230        240
VQWQHKNYLP LVLIMGVVFP TLVAGLGWGD WRGGYFYAAI LRLVFVHHAT FCVNSLAHWL

       250        260        270        280        290        300
GDGPFDDRHS PRDHFITAFV TLGEGYHNFH HQFPQDYRNA IRFYQYDPTK WVIALCAFFG

       310        320        330        340        350        360
LASHLKTFPE NEVRKGQLQM IEKRVLEKKT KLQWGTPIAD LPILSFEDYQ HACKNDNKKW

       370        380        390        400        410        420
ILLEGVVYDV ADFMSEHPGG EKYIKMGVGK DMTAAFNGGM YDHSNAARNL LSLMRVAVVE

       430        440        450        460        470        480
YGGEVEAQKK NPSMPIYGTD HAKAE*
```

FIG. 4A

```
         10        20        30        40        50
GAATTCGAGGATCCGCGTACCATGGCTCTTTCGCACTCTTGTTCGATAGC

         60        70        80        90       100
TCGTACCTTTTACTCTTCATCCTTGGTGGAACACTGCTGCCGAAGCAACT

        110       120       130       140       150
CCTCCTTTCACACCCTCGACCTCAAACAACTCGCACTCCGGATCGAAGAG

        160       170       180       190       200
TGCAGCAACGCAGGACGCACAGCGATGGCAACTCCTCTCCCCCCCTCCTT
                         M  A  T  P  L  P  P  S  F

        210       220       230       240       250
CGTCGTCCCCGCGACACAGACGGAAACCCGCAGAGATCCTCTCCAGCACG
 V  V  P  A  T  Q  T  E  T  R  R  D  P  L  Q  H  E

        260       270       280       290       300
AGGAACTGCCCCCTCTCTTCCCCGAGAAAATCACCATTTACAACATCTGG
  E  L  P  P  L  F  P  E  K  I  T  I  Y  N  I  W

        310       320       330       340       350
AGATATCTTGACTACAAGCATGTTGTTGGTCTGGGACTGACACCTTTGAT
R  Y  L  D  Y  K  H  V  V  G  L  G  L  T  P  L  I

        360       370       380       390       400
CGCACTCTACGGCCTTTTGACGACCGAGATCCAGACGAAGACCCTGATCT
 A  L  Y  G  L  L  T  T  E  I  Q  T  K  T  L  I  W

        410       420       430       440       450
GGTCCATCATCTACTACTACGCTACGGGCCTTGGTATCACAGCAGGTTAT
  S  I  I  Y  Y  Y  A  T  G  L  G  I  T  A  G  Y

        460       470       480       490       500
CATCGACTCTGGGCCCATCGTGCCTACAACGCAGGACCTGCCATGAGCTT
H  R  L  W  A  H  R  A  Y  N  A  G  P  A  M  S  F
```

FIG. 4B

```
        510        520          530        540         550
CGTACTCGCACTGCTTGGCGCTGGTGCTGTTGAAGGATCTATCAAGTGGT
 V  L  A  L  L  G  A  G  A  V  E  G  S  I  K  W  W

        560        570          580        590          600
GGTCCCGCGGCCACCGTGCTCACCACCGTTGGACAGACACCGAGAAGGAT
  S  R  G  H  R  A  H  H  R  W  T  D  T  E  K  D

        610        620          630        640         650
CCCTATAGCGCTCACCGCGGACTTTTTTCTCGCACATTGGCTGGATGCT
P  Y  S  A  H  R  G  L  F  F  S  H  I  G  W  M  L

        660        670         680        690          700
GATCAAGCGTCCTGGATGGAAGATTGGCCATGCCGATGTCGACGACCTCA
 I  K  R  P  G  W  K  I  G  H  A  D  V  D  D  L  N

        710        720         730        740          750
ACAAGAGCAAACTCGTTCAGTGGCAGCACAAGAACTACCTCCCTCTTGTT
  K  S  K  L  V  Q  W  Q  H  K  N  Y  L  P  L  V

        760        770         780        790          800
CTTATTATGGGTGTTGTCTTCCCCACACTTGTTGCTGGTCTCGGCTGGGG
L  I  M  G  V  V  F  P  T  L  V  A  G  L  G  W  G

        810        820         830        840          850
CGACTGGCGCGGAGGTTACTTCTATGCTGCCATTCTTCGTCTTGTCTTTG
 D  W  R  G  G  Y  F  Y  A  A  I  L  R  L  V  F

        860        870         880        890          900
TCCACCACGCCACCTTTTGTGTCAACTCCCTGGCTCACTGGCTCGGCGAT
V  H  H  A  T  F  C  V  N  S  L  A  H  W  L  G  D

        910        920         930        940          950
GGACCCTTTGATGACCGCCACTCCCCCCGCGACCACTTTATCACTGCCTT
G  P  F  D  D  R  H  S  P  R  D  H  F  I  T  A  F

        960        970         980        990         1000
TGTCACTTTGGGCGAAGGTTACCACAACTTCCATCACCAGTTCCCCCAGG
 V  T  L  G  E  G  Y  H  N  F  H  H  Q  F  P  Q  D
```

FIG. 4C

```
     1010      1020      1030      1040      1050
ACTACCGCAACGCTATCCGTTTCTACCAGTACGACCCTACAAAGTGGGTC
  Y  R  N  A  I  R  F  Y  Q  Y  D  P  T  K  W  V

     1060      1070      1080      1090      1100
ATTGCCCTCTGCGCTTTCTTTGGCCTCGCTTCTCACCTCAAGACCTTCCC
I  A  L  C  A  F  F  G  L  A  S  H  L  K  T  F  P

     1110      1120      1130      1140      1150
TGAGAATGAAGTTCGCAAGGGTCAGCTCCAGATGATTGAGAAGCGTGTCT
 E  N  E  V  R  K  G  Q  L  Q  M  I  E  K  R  V  L

     1160      1170      1180      1190      1200
TGGAGAAGAAGACCAAGCTTCAGTGGGGCACCCCCATTGCCGATCTGCCC
  E  K  K  T  K  L  Q  W  G  T  P  I  A  D  L  P

     1210      1220      1230      1240      1250
ATTCTGAGCTTTGAGGACTACCAGCATGCCTGCAAGAACGACAACAAGAA
I  L  S  F  E  D  Y  Q  H  A  C  K  N  D  N  K  K

     1260      1270      1280      1290      1300
GTGGATTCTATTGGAGGGCGTCGTCTACGATGTTGCTGACTTCATGTCAG
 W  I  L  L  E  G  V  V  Y  D  V  A  D  F  M  S  E

     1310      1320      1330      1340      1350
AGCACCCTGGAGGTGAGAAGTACATCAAGATGGGCGTTGGCAAGGACATG
  H  P  G  G  E  K  Y  I  K  M  G  V  G  K  D  M

     1360      1370      1380      1390      1400
ACTGCAGCCTTCAACGGCGGCATGTACGATCACAGCAACGCCGCCCGCAA
T  A  A  F  N  G  G  M  Y  D  H  S  N  A  A  R  N

     1410      1420      1430      1440      1450
CTTGCTGAGCTTGATGCGCGTTGCCGTCGTTGAGTATGGTGGTGAAGTTG
 L  L  S  L  M  R  V  A  V  V  E  Y  G  G  E  V  E

     1460      1470      1480      1490      1500
AGGCTCAGAAGAAGAACCCTTCGATGCCCATCTACGGCACTGACCACGCC
  A  Q  K  K  N  P  S  M  P  I  Y  G  T  D  H  A
```

FIG. 4D

```
        1510       1520       1530       1540       1550
AAGGCCGAATAGACGGCGAGCTGGCCTGGCCCCTTGTGCGCATTACACCA
K  A  E  *

        1560       1570       1580       1590       1600
CTATACCTCCACCCTCTCTTTTGAGTATTCTTTGTTAGTCCTACATTTCA

        1610       1620       1630       1640       1650
CATCGACTCCCTTGCAGCTATTCATGAACACATAGCTCACTCCTTGTACC

        1660       1670       1680       1690       1700
ATTTCCAACCTCCCTGCATCCTGTAATAAACACTCGTTCTACAACCGAAA

        1710       1720       1730       1740       1750
AAAAAAAAAAAAAAAAAACCATGGTACCCGGATCCTCGAATTC
```

FIG. 5A

```
        10         20         30         40         50         60
CCGACACATC CACAAGCTGC GCATGTGGCC ATTGCAGGAT GTGATTCATG AAAAATACCT

        70         80         90        100        110        120
GATGCCTCGG GCGGACGCCG ACTTTTTGGC GGACTTTCTT GGACGAATGC TGTTACTGGA

       130        140        150        160        170        180
TCCCCAGTTG CGCGCATCTG CACAGGAAAT GTCCCAGCAT CCTTGGCTGT TTGTGAAGGA

       190        200        210        220        230        240
TCCTGTGGAC GAGGAAGGCG GCGAGAGAGA CGACTTCCAG ATCAGCATGG CGACAAAGGG

       250        260        270        280        290        300
AGAGGGAGAC CGCGAGCATG CAGGAAAAAG TCCTTCCGGT GGGCGTGAAT CAAAGGCGAC

       310        320        330        340        350        360
TGAGGACGAG GAGGCGAACT TGTCAGATCA CGTCATGGAT GAAGGCGAGA ACTGAGGGTT

       370        380        390        400        410        420
CTCACATTGA ATTTGTAGCG AATAAAACGA CTTCAGACCG TTATTGTCAC AATCGCAGGA

       430        440        450        460        470        480
TGCCGATGCG AAACGAAAGT ATAAACTGGG ATGGTGTCCG AGACCGAGTT GGTCACCAAG
```

FIG. 5B

```
       490        500        510        520        530        540
AGGCGTCCAT ATCCGGACTA CCCTCTTTTG TCAGATAAAA AAAAAATATC CACCCAAAGC

       550        560        570        580        590        600
TGGTCTGTGC TTCAAAAATT TCAATTATCA ATCATTTTTG ATTCAAAAAA AAATTATTCA

       610        620        630        640        650        660
GCGGTATTCC AGTGCCCCAA AAAAAATTGC TCACCCAAAT TTTCTTCAGG CACGAAGGCC

       670        680        690        700        710        720
TGTGCGACAG GTGGATAACC ACATTACTCT TGACAAAGCA CATATCCGTG TCCGAAGATC

       730        740        750        760        770        780
GCTGTGCGCG CCCGCCCCCT GCCAAGTGTT CGATGGCACC TGTTTATCGC CGTGTCACCC

       790        800        810        820        830        840
ATCCACCGAA TCACCGAGTC CGACTGTGTC CAACTGTGCT CTAGCGCCTC ACCCACCAGG

       850        860        870        880        890        900
GTGTCAGATG GACAGCGGAG ATGTACACGC CAGTCTCCAC ATCTTTCGGT GCACTTCATC

       910        920        930        940        950        960
CCCGACTACG GATCAAAGCT CTGCTGTTCT GTGCAGTATG TGCTCTCCGT AGCTTCCTAG
```

*FIG. 5C*

```
       970        980        990       1000       1010       1020
AGCGTGGCCG ACAATCAACT GATGCTAATC GAGTAGTTGT GAATAGCATC GGACGTCCAT

      1030       1040       1050       1060       1070       1080
AGCGATACCG AGTGAATGCA AGGCTTCACC CACGACTACC AAGCTGTGCA ACCATGCTTG

      1090       1100       1110       1120       1130       1140
CGAAAGCGTT GAATTATTGA CAAACCATAA CAACTTTACG GCTTTGTGGG AGCAAGGTAG

      1150       1160       1170       1180       1190       1200
TCATAGCGAG ACCGAACGAG CTGAGGCTCA GTGCGCGTGA AAGAATGATC TTGGCTGCAA

      1210       1220       1230       1240       1250       1260
AGAAGATTGA TAGGCAGCAT TGAGTTCAGT TGCACTGTCG TCACAGACAA TTATCCTAAA

      1270       1280       1290       1300       1310       1320
CTGCTTTTTT GACTAAAGAG GCAATTATGC TGAGCAAGCA TGAACAAATG GACATGTCAA

      1330       1340       1350       1360       1370       1380
AGGGTCCTTG GAATAGCATA TTTGAGCAAG AGTGAGTTGA CTATGAGCGC ACCAGTCTAG
```

FIG. 6A

```
       1390       1400       1410       1420       1430       1440
CATTAGCGGC ACGAGCAACA CTTGGCAAGA ACACACCCCG GCTCTTGCAG TGTTGTGCAT

       1450       1460       1470       1480       1490       1500
TTGGTCAGTC AATTTTCTTG GGCGTTTGCG TTGCCTAAGT GCCTATCTGG AGTAGCTTTG

       1510       1520       1530       1540       1550       1560
TAAGATGGGA CTTGGCCTTT CATTTTTTTT ACTTTAGTTT TTTATGGGGC GCTTTTTTCG

       1570       1580       1590       1600       1610       1620
CCGTCAAGTA TATAAACCCG AAGGCACCGG ACTTTCTGCT CCTTTCTTTC ACCACCATCT

       1630       1640       1650       1660       1670       1680
CACCTTCGCC TCCCGCTTTT GGTACCACCT CTTTCGCACT CTTGTTCGAT AGCTCGTACC

       1690       1700       1710       1720       1730       1740
TTTTACTCTT CATCCTTGGT GGAACACTGC TGCCGAAGCA ACTCCTCCTT TCACACCCTC

       1750       1760       1770       1780       1790       1800
GACCTCAAAC AACTCGCACT CCGGATCGAA GAGTGCAGCA ACGCAGGACG CACAGCGATG

       1810       1820       1830       1840       1850       1860
GCAACTCCTC TCCCCCCCTC CTTCGTCGTC CCCGCGACAC AGACGGAAAC CCGCAGAGAT
```

FIG. 6B

| 1870 | 1880 | 1890 | 1900 | 1910 | 1920 |
|---|---|---|---|---|---|
| CCTCTCCAGC | ACGAGGAACT | GCCCCCTCTC | TTCCCCGAGA | AAATCACCAT | TTACAACATC |
| 1930 | 1940 | 1950 | 1960 | 1970 | 1980 |
| TGGAGATATC | TTGACTACAA | GCATGTTGTT | GGTCTGGGAC | TGACACCTTT | GATCGCACTC |
| 1990 | 2000 | 2010 | 2020 | 2030 | 2040 |
| TACGGCCTTT | TGACGACCGA | GATCCAGACG | AAGACCCTGA | TCTGGTCCAT | CATCTACTAC |
| 2050 | 2060 | 2070 | 2080 | 2090 | 2100 |
| TACGCTACGG | GCCTTGGTAT | CACAGCAGGC | AAGTTCTTAG | TGTCCCACCG | GCTCTTTTAA |
| 2110 | 2120 | 2130 | 2140 | 2150 | 2160 |
| TATAAATCAC | CGATTTCAGA | ATGTTGGGGT | CTGAGCTTTT | ATATCGTAAT | ACGCTTTTGC |
| 2170 | 2180 | 2190 | 2200 | 2210 | 2220 |
| GGCACTTGAA | TTGTTCGCTA | ACATTGAACC | CCCCACAAAT | TTCTAATTCT | CGTCAATGCA |
| 2230 | 2240 | 2250 | 2260 | 2270 | 2280 |
| GGTTATCATC | GACTCTGGGC | CCATCGTGCC | TACAACGCAG | GACCTGCCAT | GAGCTTCGTA |
| 2290 | 2300 | 2310 | 2320 | 2330 | 2340 |
| CTCGCACTGC | TTGGCGCTGG | TGCTGTTGAA | GGATCTATCA | AGTGGTGGTC | CCGCGGCCAC |

FIG. 6C

```
      2350       2360       2370       2380       2390       2400
CGTGCTCACC ACCGTTGGAC AGACACCGAG AAGGATCCCT ATAGCGCTCA CCGCGGACTT

      2410       2420       2430       2440       2450       2460
TTTTTCTCGC ACATTGGCTG GATGCTGATC AAGCGTCCTG GATGGAAGAT TGGCCATGCC

      2470       2480       2490       2500       2510       2520
GATGTCGACG ACCTCAACAA GAGCAAACTC GTTCAGTGGC AGCACAAGAA CTACCTCCCT

      2530       2540       2550       2560       2570       2580
CTTGTTCTTA TTATGGGTGT TGTCTTCCCC ACACTTGTTG CTGGTCTCGG CTGGGGCGAC

      2590       2600       2610       2620       2630       2640
TGGCGCGGAG GTTACTTCTA TGCTGCCATT CTTCGTCTTG TCTTTGTCCA CCACGCCACC

      2650       2660       2670       2680       2690       2700
TTTTGTGTCA ACTCCCTGGC TCACTGGCTC GGCGATGGAC CCTTTGATGA CCGCCACTCC

      2710       2720       2730       2740       2750       2760
CCCCGCGACC ACTTTATCAC TGCCTTTGTC ACTTTGGGCG AAGGTTACCA CAACTTCCAT
```

FIG. 7A

```
      2770       2780       2790       2800       2810       2820
CACCAGTTCC CCCAGGACTA CCGCAACGCT ATCCGTTTCT ACCAGTACGA CCCTACAAAG

      2830       2840       2850       2860       2870       2880
TGGGTCATTG CCCTCTGCGC TTTCTTTGGC CTCGCTTCTC ACCTCAAGAC CTTCCCTGAG

      2890       2900       2910       2920       2930       2940
AATGAAGTTC GCAAGGGTCA GCTCCAGATG ATTGAGAAGC GTGTCTTGGA GAAGAAGACC

      2950       2960       2970       2980       2990       3000
AAGCTTCAGT GGGGCACCCC CATTGCCGAT CTGCCCATTC TGAGCTTTGA GGACTACCAG

      3010       3020       3030       3040       3050       3060
CATGCCTGCA AGAACGACAA CAAGAAGTGG ATTCTATTGG AGGGCGTCGT CTACGATGTT

      3070       3080       3090       3100       3110       3120
GCTGACTTCA TGTCAGAGCA CCCTGGAGGT GAGAAGTACA TCAAGATGGG CGTTGGCAAG

      3130       3140       3150       3160       3170       3180
GACATGACTG CAGCCTTCAA CGGCGGCATG TACGATCACA GCAACGCCGC CCGCAACTTG

      3190       3200       3210       3220       3230       3240
CTGAGCTTGA TGCGCGTTGC CGTCGTTGAG TATGGTGGTG AAGTTGAGGC TCAGAAGAAG
```

FIG. 7B

```
        3250        3260        3270        3280        3290        3300
AACCCTTCGA  TGCCCATCTA  CGGCACTGAC  CACGCCAAGG  CCGAATAGAC  GGCGAGCTGG

        3310        3320        3330        3340        3350        3360
CCTGGCCCCT  TGTGCGCATT  ACACCACTAT  ACCTCCACCC  TCTCTTTTGA  GTATTCTTTG

        3370        3380        3390        3400        3410        3420
TTAGTCCTAC  ATTTCACATC  GACTCCCTTG  CAGCTATTCA  TGAACACATA  GCTCACTCCT

        3430        3440        3450        3460        3470        3480
TGTACCATTT  CCAACCTCCC  TGCATCCTGT  AATAAACACT  CGTTCTACAA  CCATGTGACC

        3490        3500        3510        3520        3530        3540
TAAAATGACT  GTAGACATAA  AGGACCTGAA  G
```

FIG. 8A

```
         10         20         30         40         50
CCGACACATCCACAAGCTGCGCATGTGGCCATTGCAGGATGTGATTCATG

         60         70         80         90        100
AAAAATACCTGATGCCTCGGGCGGACGCCGACTTTTTGGCGGACTTTCTT

        110        120        130        140        150
GGACGAATGCTGTTACTGGATCCCCAGTTGCGCGCATCTGCACAGGAAAT

        160        170        180        190        200
GTCCCAGCATCCTTGGCTGTTTGTGAAGGATCCTGTGGACGAGGAAGGCG

        210        220        230        240        250
GCGAGAGAGACGACTTCCAGATCAGCATGGCGACAAAGGGAGAGGGAGAC

        260        270        280        290        300
CGCGAGCATGCAGGAAAAAGTCCTTCCGGTGGGCGTGAATCAAAGGCGAC

        310        320        330        340        350
TGAGGACGAGGAGGCGAACTTGTCAGATCACGTCATGGATGAAGGCGAGA

        360        370        380        390        400
ACTGAGGGTTCTCACATTGAATTTGTAGCGAATAAAACGACTTCAGACCG

        410        420        430        440        450
TTATTGTCACAATCGCAGGATGCCGATGCGAAACGAAAGTATAAACTGGG

        460        470        480        490        500
ATGGTGTCCGAGACCGAGTTGGTCACCAAGAGGCGTCCATATCCGGACTA

        510        520        530        540        550
CCCTCTTTTGTCAGATAAAAAAAAAATATCCACCCAAAGCTGGTCTGTGC

        560        570        580        590        600
TTCAAAAATTTCAATTATCAATCATTTTTGATTCAAAAAAAAATTATTCA
```

FIG. 8B

```
        610       620       630       640       650
GCGGTATTCCAGTGCCCCAAAAAAAATTGCTCACCCAAATTTTCTTCAGG

        660       670       680       690       700
CACGAAGGCCTGTGCGACAGGTGGATAACCACATTACTCTTGACAAAGCA

        710       720       730       740       750
CATATCCGTGTCCGAAGATCGCTGTGCGCGCCCGCCCCCTGCCAAGTGTT

        760       770       780       790       800
CGATGGCACCTGTTTATCGCCGTGTCACCCATCCACCGAATCACCGAGTC

        810       820       830       840       850
CGACTGTGTCCAACTGTGCTCTAGCGCCTCACCCACCAGGGTGTCAGATG

        860       870       880       890       900
GACAGCGGAGATGTACACGCCAGTCTCCACATCTTTCGGTGCACTTCATC

        910       920       930       940       950
CCCGACTACGGATCAAAGCTCTGCTGTTCTGTGCAGTATGTGCTCTCCGT

        960       970       980       990      1000
AGCTTCCTAGAGCGTGGCCGACAATCAACTGATGCTAATCGAGTAGTTGT

       1010      1020      1030      1040      1050
GAATAGCATCGGACGTCCATAGCGATACCGAGTGAATGCAAGGCTTCACC

       1060      1070      1080      1090      1100
CACGACTACCAAGCTGTGCAACCATGCTTGCGAAAGCGTTGAATTATTGA

       1110      1120      1130      1140      1150
CAAACCATAACAACTTTACGGCTTTGTGGGAGCAAGGTAGTCATAGCGAG

       1160      1170      1180      1190      1200
ACCGAACGAGCTGAGGCTCAGTGCGCGTGAAAGAATGATCTTGGCTGCAA
```

*FIG. 8C*

```
         1210       1220       1230       1240       1250
AGAAGATTGATAGGCAGCATTGAGTTCAGTTGCACTGTCGTCACAGACAA

         1260       1270       1280       1290       1300
TTATCCTAAACTGCTTTTTTGACTAAAGAGGCAATTATGCTGAGCAAGCA

         1310       1320       1330       1340       1350
TGAACAAATGGACATGTCAAAGGGTCCTTGGAATAGCATATTTGAGCAAG

         1360       1370       1380       1390       1400
AGTGAGTTGACTATGAGCGCACCAGTCTAGCATTAGCGGCACGAGCAACA

         1410       1420       1430       1440       1450
CTTGGCAAGAACACACCCCGGCTCTTGCAGTGTTGTGCATTTGGTCAGTC

         1460       1470       1480       1490       1500
AATTTTCTTGGGCGTTTGCGTTGCCTAAGTGCCTATCTGGAGTAGCTTTG

         1510       1520       1530       1540       1550
TAAGATGGGACTTGGCCTTTCATTTTTTTTACTTTAGTTTTTTATGGGGC

         1560       1570       1580       1590       1600
GCTTTTTTCGCCGTCAAGTATATAAACCCGAAGGCACCGGACTTTCTGCT

         1610       1620       1630       1640       1650
CCTTTCTTTCACCACCATCTCACCTTCGCCTCCCGCTTTTGGTACCACCT

         1660       1670       1680       1690       1700
CTTTCGCACTCTTGTTCGATAGCTCGTACCTTTTACTCTTCATCCTTGGT

         1710       1720       1730       1740       1750
GGAACACTGCTGCCGAAGCAACTCCTCCTTTCACACCCTCGACCTCAAAC

         1760       1770       1780       1790       1800
AACTCGCACTCCGGATCGAAGAGTGCAGCAACGCAGGACGCACAGCGATG
                                                 M
```

FIG. 8D

```
        1810       1820        1830       1840       1850
GCAACTCCTCTCCCCCCCTCCTTCGTCGTCCCCGCGACACAGACGGAAAC
A  T  P  L  P  P  S  F  V  V  P  A  T  Q  T  E  T

        1860       1870        1880       1890       1900
CCGCAGAGATCCTCTCCAGCACGAGGAACTGCCCCCTCTCTTCCCCGAGA
 R  R  D  P  L  Q  H  E  E  L  P  P  L  F  P  E  K

        1910       1920        1930       1940       1950
AAATCACCATTTACAACATCTGGAGATATCTTGACTACAAGCATGTTGTT
 I  T  I  Y  N  I  W  R  Y  L  D  Y  K  H  V  V

        1960       1970        1980       1990       2000
GGTCTGGGACTGACACCTTTGATCGCACTCTACGGCCTTTTGACGACCGA
 G  L  G  L  T  P  L  I  A  L  Y  G  L  L  T  T  E

        2010       2020        2030       2040       2050
GATCCAGACGAAGACCCTGATCTGGTCCATCATCTACTACTACGCTACGG
 I  Q  T  K  T  L  I  W  S  I  I  Y  Y  Y  A  T  G

        2060       2070        2080       2090       2100
GCCTTGGTATCACAGCAGGCAAGTTCTTAGTGTCCCACCGGCTCTTTTAA
 L  G  I  T  A

       2110       2120        2130       2140       2150
TATAAATCACCGATTTCAGAATGTTGGGGTCTGAGCTTTTATATCGTAAT

       2160       2170        2180       2190       2200
ACGCTTTTGCGGCACTTGAATTGTTCGCTAACATTGAACCCCCCACAAAT

       2210       2220        2230       2240       2250
TTCTAATTCTCGTCAATGCAGGTTATCATCGACTCTGGGCCCATCGTGCC
                               Y  H  R  L  W  A  H  R  A

      2260       2270        2280       2290       2300
TACAACGCAGGACCTGCCATGAGCTTCGTACTCGCACTGCTTGGCGCTGG
Y  N  A  G  P  A  M  S  F  V  L  A  L  L  G  A  G
```

FIG. 8E

```
      2310       2320         2330      2340       2350
TGCTGTTGAAGGATCTATCAAGTCGTGGTCCCGCGGCCACCGTGCTCACC
 A  V  E  G  S  I  K  W  W  S  R  G  H  R  A  H  K

     2360       2370         2380      2390       2400
ACCGTTGGACAGACACCGAGAAGGATCCCTATAGCGCTCACCGCGGACTT
  R  W  T  D  T  E  K  D  P  Y  S  A  H  R  G  L
```

*FIG. 9A*

```
        2410      2420        2430       2440       2450
TTTTTCTCGCACATTGGCTGGATGCTGATCAAGCGTCCTGGATGGAAGAT
F  F  S  H  I  G  W  M  L  I  K  R  P  G  W  K I

        2460      2470        2480       2490       2500
TGGCCATGCCGATGTCGACGACCTCAACAAGAGCAAACTCGTTCAGTGGC
 G  H  A  D  V  D  D  L  N  K  S  K  L  V  Q  W Q

        2510      2520        2530       2540       2550
AGCACAAGAACTACCTCCCTCTTGTTCTTATTATGGGTGTTGTCTTCCCC
  H  K  N  Y  L  P  L  V  L  I  M  G  V  V  F  P

        2560      2570        2580       2590       2600
ACACTTGTTGCTGGTCTCGGCTGGGGCGACTGGCGCGGAGGTTACTTCTA
T  L  V  A  G  L  G  W  G  D  W  R  G  G  Y  F  Y

        2610      2620        2630       2640       2650
TGCTGCCATTCTTCGTCTTGTCTTTGTCCACCACGCCACCTTTTGTGTCA
 A  A  I  L  R  L  V  F  V  H  H  A  T  F  C  V  N

        2660      2670        2680       2690       2700
ACTCCCTGGCTCACTGGCTCGGCGATGGACCCTTTGATGACCGCCACTCC
  S  L  A  H  W  L  G  D  G  P  F  D  D  R  H  S

        2710      2720        2730       2740       2750
CCCCGCGACCACTTTATCACTGCCTTTGTCACTTTGGGCGAAGGTTACCA
P  R  D  H  F  I  T  A  F  V  T  L  G  E  G  Y  H

       2760      2770         2780       2790       2800
CAACTTCCATCACCAGTTCCCCCAGGACTACCGCAACGCTATCCGTTTCT
N  F  H  H  Q  F  P  Q  D  Y  R  N  A  I  R  F  Y

       2810      2820         2830       2840       2850
ACCAGTACGACCCTACAAAGTGGGTCATTGCCCTCTGCGCTTTCTTTGGC
  Q  Y  D  P  T  K  W  V  I  A  L  C  A  F  F  G

       2860      2870         2880       2890       2900
CTCGCTTCTCACCTCAAGACCTTCCCTGAGAATGAAGTTCGCAAGGGTCA
L  A  S  H  L  K  T  F  P  E  N  E  V  R  K  G  Q
```

FIG. 9B

```
       2910      2920       2930       2940       2950
GCTCCAGATGATTGAGAAGCGTGTCTTGGAGAAGAAGACCAAGCTTCAGT
 L  Q  M  I  E  K  R  V  L  E  K  K  T  K  L  Q  W

       2960      2970       2980       2990       3000
GGGGCACCCCCATTGCCGATCTGCCCATTCTGAGCTTTGAGGACTACCAG
   G  T  P  I  A  D  L  P  I  L  S  F  E  D  Y  Q

       3010      3020       3030       3040       3050
CATGCCTGCAAGAACGACAACAAGAAGTGGATTCTATTGGAGGGCGTCGT
H  A  C  K  N  D  N  K  K  W  I  L  L  E  G  V  V

       3060      3070       3080       3090       3100
CTACGATGTTGCTGACTTCATGTCAGAGCACCCTGGAGGTGAGAAGTACA
  Y  D  V  A  D  F  M  S  E  H  P  G  G  E  K  Y  I

       3110      3120       3130       3140       3150
TCAAGATGGGCGTTGGCAAGGACATGACTGCAGCCTTCAACGGCGGCATG
   K  M  G  V  G  K  D  M  T  A  A  F  N  G  G  M

       3160      3170       3180       3190       3200
TACGATCACAGCAACGCCGCCCGCAACTTGCTGAGCTTGATGCGCGTTGC
Y  D  H  S  N  A  A  R  N  L  L  S  L  M  R  V  A

       3210      3220       3230       3240       3250
CGTCGTTGAGTATGGTGGTGAAGTTGAGGCTCAGAAGAAGAACCCTTCGA
  V  V  E  Y  G  G  E  V  E  A  Q  K  K  N  P  S  M

       3260      3270       3280       3290       3300
TGCCCATCTACGGCACTGACCACGCCAAGGCCGAATAGACGGCGAGCTGG
   P  I  Y  G  T  D  H  A  K  A  E  *

       3310      3320       3330       3340       3350
CCTGGCCCCTTGTGCGCATTACACCACTATACCTCCACCCTCTCTTTTGA

       3360      3370       3380       3390       3400
GTATTCTTTGTTAGTCCTACATTTCACATCGACTCCCTTGCAGCTATTCA
```

FIG. 9C

```
       3410      3420      3430      3440      3450
TGAACACATAGCTCACTCCTTGTACCATTTCCAACCTCCCTGCATCCTGT

       3460      3470      3480      3490      3500
AATAAACACTCGTTCTACAACCATGTGACCTAAAATGACTGTAGACATAA

       3510      3520
AGGACCTGAAG
```

Δ9-DESATURASE GENE

This application is the national phase of international application PCT/JP98/00819 filed 27 Feb. 1998 which designated the U.S.

TECHNICAL FIELD

This invention relates to a gene encoding Δ9-desaturase having the activity of desaturating the Δ9-position of a fatty acid. More specifically, the invention relates to a gene encoding Δ9-desaturase of a microorganism belonging to the subgenus Mortierella of the genus Mortierella which is known to accumulate useful, highly unsaturated fatty acids, including arachidonic acid, intracellularly in marked amounts; a process for producing Δ9-desaturase using this gene; an expression vector containing this gene; a transformant transformed with the expression vector; and their utilization.

BACKGROUND ART

Unsaturated fatty acids are synthesized in animals, plants, and microorganisms. Except in higher animals, palmitic acid and stearic acid, which are saturated fatty acids, turn into monounsaturated acids having cis-Δ9 upon desaturation with oxygenases. Then, carbon chain elongation and desaturation are repeated to form unsaturated fatty acids. Such desaturation reactions are each aerobic desaturation relying on a monooxygenation reaction. A saturated fatty acid, such as palmitic acid or stearic acid, is desaturated in the presence of an oxygen atom and NAD(P)H to become a monoenoic acid.

In the present specification, a protein with the activity of desaturating the Δ9-position of a fatty acid is referred to as Δ9-desaturase. Δ9 is a designation complying with the rule that the position of a double bond of a fatty acid is expressed by Δ (delta) combined with the number of the carbon atoms ranging from the carbon atom of its terminal carboxyl group to the carbon atom where the double bond exists. Namely, Δ9 means the presence of a double bond between the 9th and the 10th carbon atom counting from the carbon atom of the terminal carboxyl group. The position of a double bond may be described subsequently to ω (omega), which represents the number of carbon atoms ranging from the carbon atom of the terminal methyl group of a fatty acid to the carbon atom where the double bond exists.

Of the so biosynthesized unsaturated fatty acids, arachidonic acid (may be designated as "ARA"), dihomo-γ-linolenic acid (may be designated as "DGLA"), and eicosapentaenoic acid (may be designated as "EPA") are precursors of physiologically active substances having various physiological actions (prostaglandins and thromboxanes). EPA, for example, is commercially available as a health food or a pharmaceutical based on its antithrombotic action or a lipid lowering action. In recent years, ARA and docosahexaenoic acid (may be designated as "DHA") has been reported to be contained in breast milk, and to be useful for the growth of an infant ("Advances in Polyunsaturated Fatty Acid Research", Elsevier Science Publishers, 1993, pp. 261–264). Their importance to the height of a fetus and the growth of its brain has also been reported (Proc. Natl. Acad. Sci. USA, 90, 1073–1077 (1993); Lancet, 344, 1319–1322 (1994)).

With this background, moves have been made to add ARA and DHA, the main sources of the difference in fatty acid composition between mother's milk and infant formula, to the infant formula.

In recent years, fish oil has been used for the purpose of adding DHA to infant formula. However, fish oil is an acylglycerol mixture containing many kinds of fatty acids as constituent fatty acids. Since isolation of these components is difficult, fish oil-containing infant formula contains a large amount of EPA as well as DHA. By the action of EPA, conversion from linoleic acid to ARA is suppressed, so that in vivo ARA is decreased. To solve this problem, attention has recently been paid to methods for producing large amounts of desired unsaturated fatty acids, without involving the incorporation of untoward fatty acids, by use of microorganisms, such as Chlorella, algae, molds (filamentous fungi), or bacteria.

DISCLOSURE OF THE INVENTION

The inventors of the present invention have focused on the fact that *Mortierella alpina,* which belongs to the subgenus Mortierella of the genus Mortierella, a genus of filamentous fungi, accumulates marked amounts of fats and oils intracellularly, and its ARA-producing ability is very high. The inventors speculated that various desaturases would be present in these filamentous fungi, and their activity would be very high. Thus, they considered cloning a gene encoding Δ9-desaturase from *Mortierella alpina,* introducing this gene into a microorganism having the ability to produce an unsaturated fatty acid, and increasing the production of an unsaturated fatty acid with the assistance of the microorganism.

BRIEF DESCRIPTION OF THE DRAWINGS

FIG. 1. (SEQ ID NO: 3) shows a cDNA coding for Δ9-desaturase from *Mortierella alpina* 1S-4 of the present invention (SEQ ID NO: 3);

FIG. 2 is a continuation of FIG. 1;

FIG. 3 shows an amino acid sequence (SEQ ID NO:4) estimated from cDNA coding for Δ9-desaturase from *Mortierella alpina* 1S-4 of the present invention;

FIG. 4 shows the correspondence between the cDNA coding for Δ9-desaturase from *Mortierella alpina* 1S-4 of the present invention and the amino acid sequence estimated therefrom;

FIG. 5 (SEQ ID NO:5) shows a genomic DNA coding for Δ9-desaturase from *Mortierella alpina* 1 S-4 of the present invention (SEQ ID NO:5);

FIG. 6 (SEQ ID NO:5) is a continuation of FIG. 5;

FIG. 7 is a continuation of FIG. 6;

FIG. 8 shows the correspondence between the genomic DNA coding for Δ9-desaturase from *Mortierella alpina* 1S-4 of the present invention and the amino acid sequence encoded thereby;

FIG. 9 is a continuation of FIG. 8; and

BEST MODE FOR CARRYING OUT THE INVENTION

Figure 10:
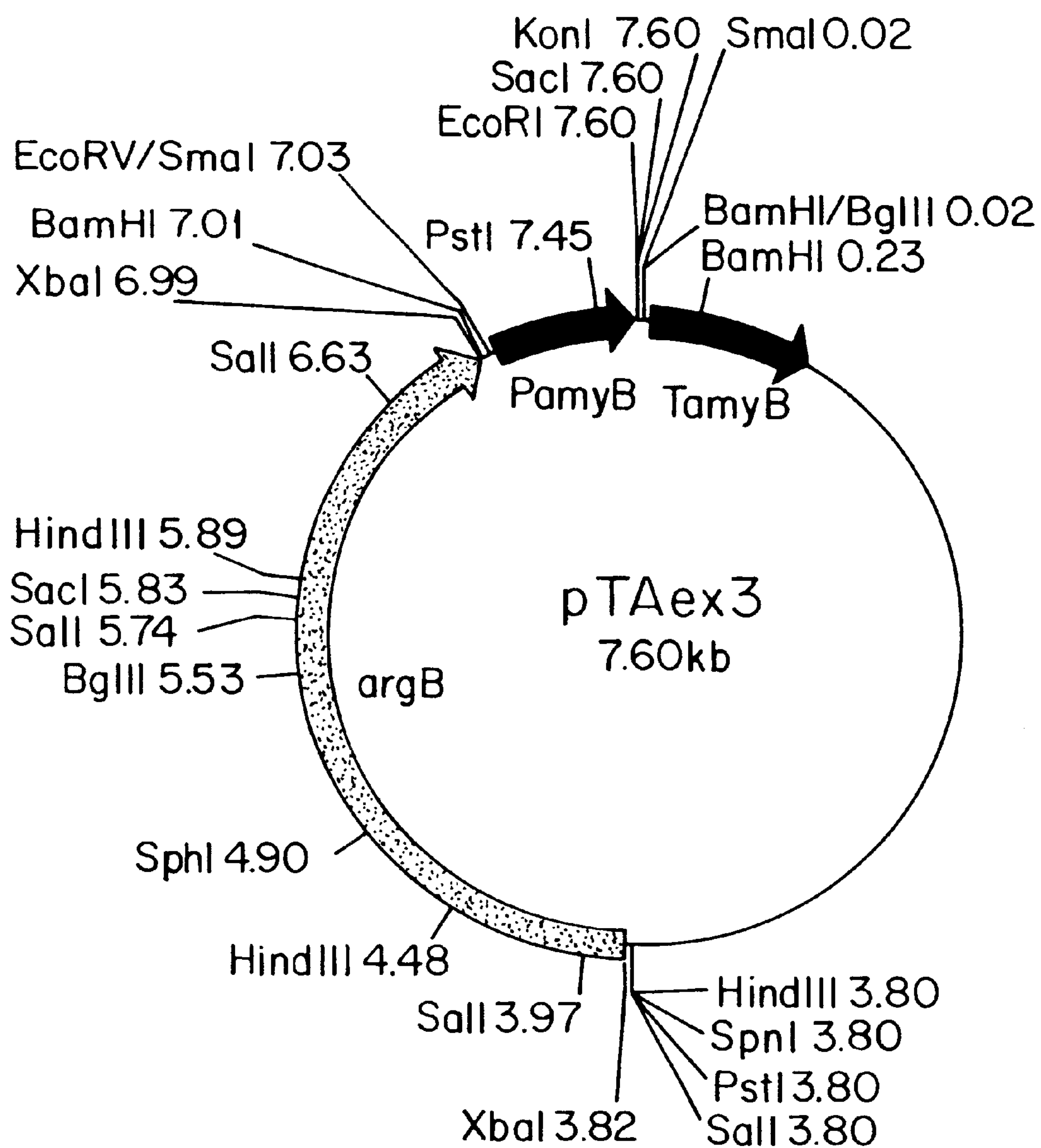
FIG. 10 shows a restriction map of a vector, pTAex3, used for constructing an expression vector in Example 3.

In the present invention, success was achieved in cloning a genomic gene and a CDNA coding for Δ9-desaturase from *Mortierella alpina* (microorganism as a source of the gene) by use of a probe prepared from primers of Seq. ID Nos. 1 and 2 of the attached Sequence Listing.

By introducing the gene of the present invention into a cell having an unsaturated fatty acid-producing ability, it can be expected that conversion from palmitic acid or stearic acid to palmitoleic acid or oleic acid, the starting material for an unsaturated fatty acid, can be enhanced, and the production of the unsaturated fatty acid can be increased. Particularly by introducing the gene of the present invention in combination with an enzyme of an electron transport system or a gene coding for other desaturase, production of the unsaturated fatty acid can be expected to increase further.

The gene of the present invention can construct a suitable expression vector by a gene recombination technology. A host cell having an unsaturated fatty acid producing ability is transformed with the expression vector. The transformant is cultured to produce the desired Δ9-unsaturated fatty acid. Such a host cell is not restricted, as long as it has the ability to produce an unsaturated fatty acid. Its examples include bacteria such as *Escherichia coli* and *Bacillus subtilis,* Basidiomycota such as Saccharomyces, and filamentous fungi such as Aspergillus. These host cells may have been transformed so as to produce unsaturated fatty acids efficiently. By introducing the gene of the present invention into higher plants producing unsaturated fatty acids, such as soybean, sunflower, rape, and sesame, by the customary method, the desired Δ9-unsaturated fatty acids can be produced.

The present invention provides a gene from a microorganism belonging to the subgenus Mortierella of the genus Mortierella, which encodes Δ9-desaturase. This gene may be cDNA from mRNA, genomic DNA, or chemically synthesized DNA. The present invention also includes a gene encoding a modified polypeptide which retains Δ9-desaturase activity, and in which one or more amino acids of an amino acid sequence of Δ9-desaturase have been deleted, in which one or more amino acids of the amino acid sequence of Δ9-desaturase have been substituted, or in which one or more other amino acids have been added to the amino acid sequence of Δ9-desaturase.

The present invention also provides a method for producing complete-length Δ9-desaturase, and a modified polypeptide by a recombinant DNA technique using a gene encoding Δ9-desaturase, the modified polypeptide which retains Δ9-desaturase activity, and in which one or more amino acids of an amino acid sequence of Δ9-desaturase have been deleted, in which one or more amino acids of the amino acid sequence of Δ9-desaturase have been substituted, or in which one or more other amino acids have been added to the amino acid sequence of Δ9-desaturase.

The Δ9-desaturase gene of the present invention can be cloned in the following manner:

Gene Source

Microorganisms which can be used as sources of the gene in the present invention are not restricted to particular species or strains, as long as they belong to the subgenus Mortierella of the genus Mortierella. For example, the following species which belong to the genus Mortierella can be named: *alpina, bainieri, elongata, exigua, minutissima, verticillata, hygrophila, and polycephala.* Strains belonging to *Mortierella alpina* can be obtained from prescribed deposition organizations under the following deposition numbers:

*Mortierella alpina* (ATCC8979, ATCC16266, ATCC32221, ATCC32222, ATCC32223, ATCC36965, ATCC42430, CBS219.35, CBS224.37, CBS250.53, CBS343.66, CBS527.72, CBS529.72, CBS608.70, CBS754.68, IFO8568, IFO32281).

In the present invention, an organism having the ability to produce an unsaturated fatty acid is transformed, whereby the organism with enhanced Δ9-desaturase activity can be created artificially.

Examples of the organism having the unsaturated fatty acid producing ability are microorganisms having omega-3 unsaturated fatty acid producing ability, and microorganisms having omega-6 unsaturated fatty acid producing ability. The microorganisms having omega-3 unsaturated fatty acid producing ability include, for example, marine Chlorella, fine red algae, and fine algae, e.g., genera belonging to Chromophyt, such as Crypthecodinium, Isochrysis, Nannochloropsis, Chaetoceros, Phaeodactylum, Amphidinium, Gonyaulax, Peridimium, Chroomonas, Cryptomonas, Hemiselmis, and Chilomonas, Chlorella belonging to Chlorophyta, Histiobranchus, and Coryphaenoides. Among Crypthecodimium, *Crypthecodimium cohnii* ATCC30021, for instance, can be cited. This strain is available, without limitation, from the American Type Culture Collection. Furthermore, marine bacteria, which have been isolated from the intestine of a mackerel producing oils and fats with a high eicosapentaenoic acid content (genus Shewanella, e.g., *Shewanella putrefaciens*), can be named.

The microorganisms having omega-6 unsaturated fatty acid producing ability include, for example, γ-linolenic acid-producing microorganisms, and arachidonic acid-producing microorganisms. Examples of the arachidonic acid-producing microorganisms are species of the subgenus Mortierella of genus Mortierella, such as *alpina, bainieri, elongata, exigua, minutissima, verticillata, hygrophila,* and *polycephala,* and microorganisms of the genera Conidiobolus, Phythium, Phytophthora, Penicillium, Cladosporium, Mucor, Fusarium, Aspergillus, Rhodotorula, Entomophthora, Echinosporangium, and Saprolegnia. Examples of the γ-linolenic acid-producing microorganisms are species of the subgenus Micromucor of genus Mortierella, such as *isabellina, vinacea, ramaniana var. ramaniana, ramaniana var. anglispora,* and *nana,* and microorganisms of the genera Absidia, Mucor, Rizopus, Syncephalastrum, and Choanephora. Among strains of subgenus Mortierella of genus Mortierella, the following can be named: *Mortierella elongata* IFO8570, *Mortierella exigua* IFO8571, *Mortierella hygrophila* IFO5941, *Mortierella alpina* ATCC8979, ATCC16266, ATCC32221, ATCC32222, ATCC32223, ATCC36965, ATCC42430, CBS219.35, CBS224.37, CBS250.53, CBS343.66, CBS527.72, CBS529.72, CBS608.70, CBS754.68, IFO8568, and IFO32281. These strains can be obtained, without any restriction, from the Fermentation Research Institute. The strain *Mortierella elongata* SAM0219 (FERM Deposition No. 8703)(FERM BP-1239), isolated by the inventors from the soil, may also be used.

Cloning of Δ9-desaturase Genomic DNA

① Extraction of Genomic DNA of Microorganism Belonging to Subgenus Mortierella of Genus Mortierella, and Preparation of Cosmid Library Cells of a microorganism belonging to subgenus Mortierella of genus Mortierella, which have been cultured and harvested, are crushed. By the customary methods, chromosomal DNA is centrifuged and precipitated, RNA is decomposed and removed, and proteins are eliminated to purify the DNA components. For these steps, reference is requested to "Plant Biotechnology Experiment Manual, Noson-Bunkasha, page 252".

A commercially available cosmid vector kit is used to insert the above genomic DNA as an insert DNA into a cosmid vector in accordance with the attached Instructions. The resulting recombinant vector is packaged using a bacterium extract attached to a commercially available packaging kit, and a host cell is infected with the package. The infected host cell is proliferated to construct a cosmid library.

② Preparation of Probe

Based on rat and yeast Δ9-desaturase cDNA sequences whose estimated amino acid sequences show relatively high homology among the known Δ9-desaturases, a sense primer and an antisense primer are prepared. These primers are used to perform PCR using, as a template, genomic DNA of a microorganism belonging to subgenus Mortierella of genus Mortierella. The resulting amplified DNA fragments are sequenced, and converted to an amino acid sequence, which is confirmed to have homology to Δ9-desaturases from other organisms, and which is confirmed to contain a sequence homologous to a partial amino acid sequence of the above-described internal peptide. The confirmed sequence is labeled with an isotope, and used as a probe for subsequent experiments.

③ Cloning from Cosmid Library

The foregoing probe is used for colony hybridization to the aforementioned cosmid library. The cosmid of the resulting positive clones is prepared, for example, by the alkali method, and subjected to Southern hybridization with a suitable restriction enzyme. A DNA fragment obtained as a positive band is sequenced to clone the desired genomic DNA.

Cloning of Δ9-desaturase cDNA

① Preparation of mRNA and Construction of cDNA Library

Cells of a Microorganism Belonging to Subgenus Mortierella of genus Mortierella, which have been cultured and harvested, are crushed. All RNA's are extracted by the AGPC method, and mRNA is purified from the extract by a suitable method, e.g., using an oligo(dT)-cellulose column.

From the resulting mRNA as a template, cDNA is synthesized, and then inserted into a commercially available phage vector, which is further packaged in the customary manner.

② Cloning of Δ9-desaturase cDNA

A host bacterium is infected with the above packaged cDNA library, and positive plaques are obtained by plaque hybridization. The resulting clones are sequenced, and converted to amino acid sequences for study. Studies can confirm the cloning of the entire length of Δ9-desaturase gene of the microorganism belonging to subgenus Mortierella of genus Mortierella.

③ Expression of Δ9-desaturase

Then, Δ9-desaturase is expressed using the cloned Δ9-desaturase cDNA. The expression of Δ9-desaturase can be performed by a publicly known recombinant DNA technique which inserts the Δ9-desaturase cDNA into a suitable plasmid, transforms *E. coli* as a host with the inserted plasmid, and cultures the *E. coli.* For example, the intended cDNA is inserted into a pET system having a T7 promotor, and *E. coli.* BL21 (DE3) strain is transformed with this expression plasmid. Then, the transformed *E. coli* is cultured in a suitable culture medium, and cultured cells are harvested. The cells are crushed to separate and purify Δ9-desaturase protein.

Also, the cloned Δ9-desaturase cDNA is used on a vector system for a filamentous fungus, e.g., the koji mold *Aspergillus oryzae,* to construct an expression vector suitable for expression in a microorganism belonging to the filamentous fungus. This expression vector is transformed into a filamentous fungus, e.g., *Aspergillus oryzae,* by the customary method, and clones with high efficiency of conversion from stearic acid to oleic acid are sifted out to obtain the transformed filamentous fungus.

The transformant was cultured, and total lipids were extracted for analysis. The proportions of the desired unsaturated fatty acids were confirmed to be higher than when wild type microorganisms were similarly cultured. This is proof that the introduced Δ9-desaturase gene is expressed in the transformed cells.

The present invention will be described in more detail by way of the following Examples.

EXAMPLE 1

Cloning of Genomic DNA (1) Method for extracting genomic DNA of *Mortierella alpina* 1S-4 (see "Plant Biotechnology Experiment Manual, Noson-Bunkasha, page 252".)

Cells in the latter stage of the logarithmic growth phase were harvested by vacuum filtration. The cells were frozen in liquid nitrogen, and then crushed with a homogenizer (whirling blender). The resulting crushed matter was transferred into a mortar, and mashed with the addition of liquid nitrogen. The mashed material was kept at 70° C., and suspended in 2% hexadecyl trimethyl ammonium bromide (CTAB) solution, followed by incubating the suspension for 3 to 4 hours at 65° C. The supernatant obtained by centrifugation was treated with phenol, phenol-chloroform, and chloroform in this order. DNA was precipitated with an equal volume of isopropanol, washed with 70% ethanol, air-dried, and then dissolved in TE (10 mM Tris-HCl (pH 8.0)+1 mM EDTA (pH 8.0)). The solution was treated with ribonuclease A and ribonuclease T1 to decompose RNA. Then, the treated solution was treated with phenol, phenol-chloroform, and chloroform for deproteinization. DNA was precipitated with an equal volume of isopropanol, washed with 70% ethanol, air-dried, and then dissolved in TE to obtain a genomic DNA preparation.

(2) Method for Constructing Cosmid Library

For a cosmid, SUPERCOS 1 COSMID VECTOR KIT of STRATAGENE was used. A cosmid library was prepared in accordance with its protocol. The cosmid was restriction enzyme treated with XbaI, dephosphorylated with CIP (TAKARA), and restriction enzyme treated with BamHI to prepare a cosmid arm. An insert DNA was obtained by partial digestion with the restriction enzyme Sau3AI. The cosmid arm and the partially digested insert DNA were ligated, and subjected to a next step, packaging. For packaging, GIGAPACK II PACKAGING EXTRACT of STRATAGENE was used. XL1-Blue MR was used as host a host strain of *E. coli.*

(3) Preparation of Probe

Based on rat liver and yeast Δ9-desaturase cDNA sequences whose estimated amino acid sequences show relatively high homology among the known Δ9-desaturases, a sense primer and an antisense primer were prepared. These primers were used to perform PCR using, as a template, the genomic DNA of *Mortierella alpina* 1S-4.

| Conditions for PCR | |
|---|---|
| Chromosomal DNA | 5 μg |
| Sense primer | 200 pmol |
| Antisense primer | 200 pmol |
| dNTP (2 mM) | 10 μl |
| Tth polymerase buffer (×10) | 10 μl |
| Tth DNA polymerase | 4 units |
| $H_2O$ | |
| Total | 100 μl |

[95° C. - 1 min, 55° C. - 1 min, 72° C. - 2 min: 35 cycles]

The amplified DNA fragment of about 560 bp was cloned, and its nucleotide sequence was determined. Its estimated amino acid sequence showed high homology of about 48% to the yeast Δ9-desaturase. Thus, this fragment was labeled with α-$^{32}$P-dCTP, and used as a probe for the cloning of Δ9-desaturase genomic gene and cDNA of *Mortierella alpina* 1S-4.

The resulting synthetic oligonucleotide primers were as follows:

Sense Primer 27 mer, 384 variants

```
                   Ala
   Ile Thr Ala Gly Tyr His Arg Leu Trp
5' ATAACIGCIGGIGAICACAGICTATGG 3'
     C         TC   TC  T C
     T                    G
                          T
```

Antisense Primer 26 mer, 256 variants.

```
              Phe         Phe
   His His Tyr Asn His Tyr Gly Glu Gly
5' TGATGAAAATTATGAAAICCCTCICC 3'
     G  GT G  G  GT    T
```

Notes: I denotes inosine.

(4) Cloning of Δ9-desaturase genomic gene of *Mortierella alpina* 1S-4

The cosmid library was colony hybridized using the aforementioned probe to obtain several positive clones. A cosmid of one of these positive clones was prepared by the alkali method, and subjected to Southern hybridization. The nucleotide sequence of an SI fragment of about 3.5 kb, obtained as a positive band, was determined, and thereby found to contain the entire Δ9-desaturase gene.

Example 2

Cloning of cDNA (1) Preparation of mRNA

Cells were harvested in the former stage of the logarithmic growth phase, immediately frozen in liquid nitrogen, and then crushed, whereafter all RNA's were extracted by the AGPC method. All the RNA's were applied to an oligo(dT)-cellulose column to purify mRNA (mRNA purification kit, Pharmacia Biotech).

(2) Construction of cDNA Library

The resulting mRNA was used as a template to synthesize cDNA by use of a cDNA rapid adaptor ligation module (Amersham). Then, this cDNA was ligated to λgt10 by means of a cDNA rapid cloning module-λgt10 (Amersham). This λgt10-cDNA library was packaged using a λDNA in vitro packaging module (Amersham).

(3) Cloning of Δ9-desaturase cDNA of *Mortierella alpina* 1S-4

The cDNA library was subjected to plaque hybridization using the aforementioned probe to obtain several positive plaques. Using one of these positive plaques, λ phage was prepared, and subcloned into pBluescript II to determine the nucleotide sequence.

(4) Analysis of Δ9-desaturase Gene of *Mortierella alpina* 1S-4

Based on the nucleotide sequence of Δ9-desaturase cDNA of *Mortierella alpina* 1S-4, Δ9-desaturase was estimated to comprise 446 amino acids and have a molecular weight of 50,780. This Δ9-desaturase showed high homology of 44.5% to yeast Δ9-desaturase over 402 amino acids. Based on the nucleotide sequence of the genomic gene, this Δ9-desaturase was found to contain only one intron.

(5) Expression of Δ9-desaturase

*E. coli.* was transformed with the resulting Δ9-desaturase cDNA, and the expression of Δ9-desaturase was confirmed.

EXAMPLE 3

Construction of Expression Vector (1) Construction of Vector and Transformation into Koji Mold A host vector system consisting of the vector pTAex3 and the koji mold host *Aspergillus oryzae* M-2-3 (argB-, w) was used.

PCR was performed using the following two synthetic oligonucleotide primers (sense primer (SEQ ID NO:6))

5' CAGGAATTCCCGCCATGGCAACTCCTC 3'

(antisense primer (SEQ ID NO:7))

5' GCCAGCCCGGGTCGCCGTCTATTCGGC 3' and cDNA of Δ9-desaturase of *Mortierella alpina* 1S-4. The resulting amplified DNA fragment was inserted into TA cloning vector pCR2.1 (Invitrogen) to confirm the nucleotide sequence. A DNA fragment obtained by treating this plasmid with EcoRI was inserted into an ERI site of pTAex3 (FIG. 11) to construct an expression vector.

(2) Preparation of Wild Type Strain and Transformant

*Aspergillus oryzae* M-2-3 transformed only with pTAex3 was used as a wild type strain. This organism was cultured for 3 days at 30° C. at 120 rpm in 4 ml of a culture medium (pH 5.8) containing 2% glucose or maltose, 1% polypeptone, and 0.5% yeast extract in a 20 ml Erlenmeyer flask. Cells were collected by filtration through a glass filter (3G1), and washed with sterilized water.

The cells were pressed with a spatula for dehydration, and taken into a 50 ml plastic tube. With the addition of 10 ml of a protoplast forming solution (5 mg/ml Novazym 234, 5 mg/ml Cellulase Onozuka R-10, 0.8 M NaCl, 10 mM Phosphate buffer, pH 6.0) that had been filtered through a 0.45 μm filter, the cells were suspended. The suspension was reacted for about 2 hours, with gentle stirring at 30° C. Then, the reaction mixture was filtrated through a glass filter (3G2), and the protoplast was recovered by low speed centrifugation (2,000 rpm, 5 min). The recovered product was washed twice with 0.8 M NaCl, and centrifuged to obtain protoplast.

The protoplast was suspended in Sol I (0.8 M NaCl, 10 mM Tris-HCl, pH 8.0) to a concentration of $2 \times 10^8$ cells/ml. Then, 0.2×Sol II (40% (w/v) PEG 4,000, 50 mM $CaCl_2$, 50 mM Tris-HCl, pH 8.0) was added, and mixed with the suspension.

The protoplast mixture (0.2 ml) was dispensed into a plastic tube. A solution of the expression vector prepared in (1) (up to 20 μl, 20 μg as the amount of DNA) was added, and the mixture was allowed to stand for 30 minutes in ice. Then, 1 ml of Sol II was added, and the mixture was allowed to stand for 20 minutes at room temperature. Then, 10 ml of Sol I was added, and the mixture was centrifuged at a low speed (2,000 rpm, 5 min) to precipitate protoplast. The supernatant was removed, and 0.2 ml of Sol I was added, followed by uniformly suspending the protoplast. The suspension was placed on the center of a minimal medium (Glucose 2%, $NaNO_3$ 0.2%, $KH_2PO_4$ 0.1%, KCl 0.05%, $MgSO_4.7H_2O$ 0.05%, $FeSO_4.7H_2O$ 0.01%). Then, 5 ml of a soft agar medium warmed to about 45° C. was poured over the suspension to form a uniform suspension of the protoplast rapidly.

To the resulting colonies, colony hybridization was performed, using Δ9-desaturase gene as a probe, in accordance with the customary method to obtain several clones. Of these clones, clone ES-12 strain with the highest efficiency of conversion from stearic acid to oleic acid was obtained. Genomic Southern hybridization of the ES-12 strain using the present enzyme gene as a probe gave positive bands. pTAex3 contains a promotor which is induced and expressed in *Aspergillus oryzae* when the carbon source is maltose, so that maltose was used as the source of carbon.

(3) Comparison of Fatty Acid Composition

The test strain was cultured for 3 days at 30° C. at 120 rpm in a culture medium (pH 5.8) containing 2% glucose or maltose, 1% polypeptone, and 0.5% yeast extract. Then, total lipids were extracted from dried cells, and methylated by the customary methods, analyzed by gasliquidchromatography. Compared with the wild type strain, the ES-12 strain was high in the proportions of palmitoleic acid and oleic acid, and low in the proportions of linoleic acid and α-linolenic acid. With the ES-12 strain, moreover, maltose was considered to enable a desaturation reaction from palmitic acid to palmitoleic acid, or from stearic acid to oleic acid, to proceed more rapidly than did glucose. When maltose was the carbon source, the oleic acid/stearic acid ratio was 6.9 for the wild type strain, while it was 48 for the ES-12 strain, i.e., 7 times the value for the wild type strain (see Table 1 below).

(4) Analysis of each Lipid Fraction by TLC

The test strain was cultured for 3 days at 30° C. at 120 rpm in 60 ml of a culture medium (pH 5.8) containing 2% maltose, 1% polypeptone, and 0.5% yeast extract in a 300 ml Erlenmeyer flask. From the cells harvested, total lipids were extracted by the chloroform-methanol method.

In accordance with the TLC analysis method (TLC plate), neutral lipid fractions, i.e., triacylglycerol (TG), free fatty acid (FA), diacylglycerol (DG), and phospholipid (PL), and polar lipid fractions, i.e., phosphatidyl ethanolamine (PE), phosphatidyl amine (PA), phosphatidyl choline (PC), and phosphatidyl serine (PS), were fractionated. Each fraction was methylated, and its fatty acid composition was analyzed by gasliquidchromatography. The ES-12 strain was higher in the proportion of TG, and lower in the proportion of PE, than the wild type strain. In regard to the fatty acid composition of each fraction, the ES-12 strain was higher in the proportions of palmitoleic acid and oleic acid, and lower in the proportion of linoleic acid, than the wild type strain (see Table 2 below).

TABLE 1

| Strain | Fatty acid production (μg/ml) | Fatty acid composition (mol %) | | | | | |
|---|---|---|---|---|---|---|---|
| | | 16:0 | 16:1 | 18:0 | 18:1 | 18:2 | 18:3 (n-3) |
| Wild type strain | | | | | | | |
| Glucose | 332.1 | 14.7 | 0.4 | 5.3 | 13.4 | 62.4 | 3.9 |
| Maltose | 362.6 | 15.7 | 0.4 | 1.8 | 12.4 | 64.6 | 5.1 |
| ES-12 | | | | | | | |
| Glucose | 357.9 | 9.4 | 1.3 | 4.3 | 20.7 | 59.1 | 2.5 |
| Maltose | 373.6 | 8.2 | 2.6 | 0.6 | 28.8 | 58.2 | 1.6 |

TABLE 2

| Lipid | Lipid composition (mol %) | Fatty acid composition (mol %) | | | | | |
|---|---|---|---|---|---|---|---|
| | | 16:0 | 16:1 | 18:0 | 18:1 | 18:2 | 18:3 (n-3) |
| Wild type | | | | | | | |
| TG | 25.5 | 11.8 | 0.6 | 4.3 | 14.8 | 64.4 | 4.1 |
| FA | 13.3 | 21.6 | 0.4 | 2.7 | 13.5 | 58.3 | 3.5 |
| PE | 14.3 | 28.2 | 0.3 | 1.6 | 15.0 | 53.5 | 1.4 |
| PC | 32.7 | 8.4 | 0.5 | 1.4 | 13.0 | 73.8 | 2.9 |
| PS | 5.5 | 27.0 | 0.3 | 4.3 | 16.9 | 48.7 | 2.8 |
| PA | 8.8 | 26.5 | 0.4 | 2.0 | 13.9 | 55.3 | 1.9 |
| ES-12 | | | | | | | |
| TG | 34.6 | 7.1 | 2.4 | 3.4 | 28.4 | 55.6 | 3.0 |
| FA | 21.2 | 15.6 | 1.9 | 2.4 | 23.6 | 53.6 | 3.1 |
| PE | 5.8 | 26.8 | 1.4 | 3.0 | 25.5 | 41.6 | 1.7 |
| PC | 25.1 | 5.6 | 1.9 | 2.6 | 26.4 | 61.0 | 2.4 |
| PS | 4.0 | 22.9 | 1.8 | 5.2 | 22.7 | 46.3 | 1.1 |
| PA | 9.3 | 21.1 | 1.5 | 2.7 | 23.9 | 49.3 | 1.7 |

Industrial Availability

The present invention gives a genomic DNA and a cDNA encoding Δ9-desaturase from a microorganism belonging to subgenus Mortierella of genus Mortierella which accumulates ARA intracellularly in a marked amount. By cloning the Δ9-desaturase gene, Δ9-desaturase protein can be produced by genetic engineering. Also, by transforming a microbial cell and a plant cell with this gene, increases in the production of unsaturated fatty acids in these transformants can be expected.

What is claimed is:

1. An isolated or purified DNA sequence encoding the amino acid sequence of Seq. ID No. 4.

2. An isolated or purified DNA sequence of Seq. ID No. 3.

3. An isolated or purified DNA sequence comprising a DNA sequence of Seq. ID No. 5.

4. A purified or isolated polypeptide comprising the amino acid sequence of Seq. ID No. 4.

5. A purified or isolated polypeptide encoded by the DNA sequence according to claim 2.

6. A purified or isolated polypeptide with an activity of desaturating a Δ9-position of fatty acid, wherein said polypeptide is derived from a microorganism *Mortierella alpina.*

7. An isolated or purified DNA sequence derived from a microorganism *Mortierella alpina,* which encodes Δ9-desaturase.

8. A method for desaturating the Δ9 position of a fatty acid, said method comprising:

providing a culture medium containing a fatty acid, Δ9 of which is saturated, and culturing a transformed cell in the culture medium, wherein said transformed cells are transformed with a recombinant expression vector incorporating the DNA sequence as claimed in any one of claims 1, 2, 3, and 7.

* * * * *

SEQUENCE LISTING

```
<160> NUMBER OF SEQ ID NOS: 9

<210> SEQ ID NO 1
<211> LENGTH: 27
<212> TYPE: DNA
<213> ORGANISM: Mortierella alpina
<220> FEATURE:
<221> NAME/KEY: primer_bind
<222> LOCATION: n is located at positions (6), (9), (15), (21), and (24)
<223> OTHER INFORMATION: primer DNA for PCR; h is a or c or t; n is a or
      g or c or t;
<223> OTHER INFORMATION: k is g or t; m is a or c; y is c or t

<400> SEQUENCE: 1
```

-continued

```
athacngcng gtkmncaymg nytntgg                                          27


<210> SEQ ID NO 2
<211> LENGTH: 26
<212> TYPE: DNA
<213> ORGANISM: Mortierella alpina
<220> FEATURE:
<221> NAME/KEY: primer_bind
<222> LOCATION: n is located at positions (18) and (24)
<223> OTHER INFORMATION: primer DNA for PCR; y is c or t; n is a or g or
      c or t;
<223> OTHER INFORMATION: r is a or g; w is a or t

<400> SEQUENCE: 2

tgrtgrwart trtgrwancc ytcncc                                           26


<210> SEQ ID NO 3
<211> LENGTH: 1744
<212> TYPE: DNA
<213> ORGANISM: Mortierella alpina

<400> SEQUENCE: 3

gaattcgagg atccgggtac catggctctt tcgcactctt gttcgatagc tcgtaccttt     60

tactcttcat ccttggtgga acactgctgc cgaagcaact cctcctttca caccctcgac    120

ctcaaacaac tcgcactccg gatcgaagag tgcagcaacg caggacgcac agcgatggca    180

actcctctcc cccctcctt cgtcgtcccc gcgacacaga cggaaacccg cagagatcct     240

ctccagcacg aggaactgcc ccctctcttc cccgagaaaa tcaccattta caacatctgg    300

agatatcttg actacaagca tgttgttggt ctgggactga cacctttgat cgcactctac    360

ggcctttttga cgaccgagat ccagacgaag accctgatct ggtccatcat ctactactac   420

gctacgggcc ttggtatcac agcaggttat catcgactct gggcccatcg tgcctacaac    480

gcaggacctg ccatgagctt cgtactcgca ctgcttggcg ctggtgctgt tgaaggatct    540

atcaagtggt ggtcccgcgg ccaccgtgct caccaccgtt ggacagacac cgagaaggat    600

ccctatagcg ctcaccgcgg actttttttc tcgcacattg gctggatgct gatcaagcgt    660

cctggatgga agattggcca tgccgatgtc gacgacctca acaagagcaa actcgttcag    720

tggcagcaca agaactacct ccctcttgtt cttattatgg gtgttgtctt ccccacactt    780

gttgctggtc tcggctgggg cgactggcgc ggaggttact tctatgctgc cattcttcgt    840

cttgtctttg tccaccacgc caccttttgt gtcaactccc tggctcactg gctcggcgat    900

ggaccctttg atgaccgcca ctcccccccgc gaccacttta tcactgcctt tgtcactttg   960

ggcgaaggtt accacaactt ccatcaccag ttcccccagg actaccgcaa cgctatccgt   1020

ttctaccagt acgaccctac aaagtgggtc attgccctct gcgctttctt tggcctcgct   1080

tctcacctca agaccttccc tgagaatgaa gttcgcaagg gtcagctcca gatgattgag   1140

aagcgtgtct tggagaagaa gaccaagctt cagtggggca cccccattgc cgatctgccc   1200

attctgagct ttgaggacta ccagcatgcc tgcaagaacg acaacaagaa gtggattcta   1260

ttggagggcg tcgtctacga tgttgctgac ttcatgtcag agcaccctgg aggtgagaag   1320

tacatcaaga tgggcgttgg caaggacatg actgcagcct tcaacggcgg catgtacgat   1380

cacagcaacg ccgcccgcaa cttgctgagc ttgatgcgcg ttgccgtcgt tgagtatggt   1440

ggtgaagttg aggctcagaa gaagaaccct tcgatgccca tctacggcac tgaccacgcc   1500

aaggccgaat agacggcgag ctggcctggc cccttgtgcg cattacacca ctatacctcc   1560

accctctctt ttgagtattc tttgttagtc ctacatttca catcgactcc cttgcagcta   1620
```

-continued

```
ttcatgaaca catagctcac tccttgtacc atttccaacc tccctgcatc ctgtaataaa   1680

cactcgttct acaaccgaaa aaaaaaaaaa aaaaaaaaac catggtaccc ggatcctcga   1740

attc                                                                1744


<210> SEQ ID NO 4
<211> LENGTH: 445
<212> TYPE: PRT
<213> ORGANISM: Mortierella alpina

<400> SEQUENCE: 4

Met Ala Thr Pro Leu Pro Pro Ser Phe Val Val Pro Ala Thr Gln Thr
  1               5                  10                  15

Glu Thr Arg Arg Asp Pro Leu Gln His Glu Glu Leu Pro Pro Leu Phe
             20                  25                  30

Pro Glu Lys Ile Thr Ile Tyr Asn Ile Trp Arg Tyr Leu Asp Tyr Lys
         35                  40                  45

His Val Val Gly Leu Gly Leu Thr Pro Leu Ile Ala Leu Tyr Gly Leu
     50                  55                  60

Leu Thr Thr Glu Ile Gln Thr Lys Thr Leu Ile Trp Ser Ile Ile Tyr
 65                  70                  75                  80

Tyr Tyr Ala Thr Gly Leu Gly Ile Thr Ala Gly Tyr His Arg Leu Trp
                 85                  90                  95

Ala His Arg Ala Tyr Asn Ala Gly Pro Ala Met Ser Phe Val Leu Ala
            100                 105                 110

Leu Leu Gly Ala Gly Ala Val Glu Gly Ser Ile Lys Trp Trp Ser Arg
        115                 120                 125

Gly His Arg Ala His His Arg Trp Thr Asp Thr Glu Lys Asp Pro Tyr
    130                 135                 140

Ser Ala His Arg Gly Leu Phe Phe Ser His Ile Gly Trp Met Leu Ile
145                 150                 155                 160

Lys Arg Pro Gly Trp Lys Ile Gly His Ala Asp Val Asp Asp Leu Asn
                165                 170                 175

Lys Ser Lys Leu Val Gln Trp Gln His Lys Asn Tyr Leu Pro Leu Val
            180                 185                 190

Leu Ile Met Gly Val Val Phe Pro Thr Leu Val Ala Gly Leu Gly Trp
        195                 200                 205

Gly Asp Trp Arg Gly Gly Tyr Phe Tyr Ala Ala Ile Leu Arg Leu Val
    210                 215                 220

Phe Val His His Ala Thr Phe Cys Val Asn Ser Leu Ala His Trp Leu
225                 230                 235                 240

Gly Asp Gly Pro Phe Asp Asp Arg His Ser Pro Arg Asp His Phe Ile
                245                 250                 255

Thr Ala Phe Val Thr Leu Gly Glu Gly Tyr His Asn Phe His His Gln
            260                 265                 270

Phe Pro Gln Asp Tyr Arg Asn Ala Ile Arg Phe Tyr Gln Tyr Asp Pro
        275                 280                 285

Thr Lys Trp Val Ile Ala Leu Cys Ala Phe Phe Gly Leu Ala Ser His
    290                 295                 300

Leu Lys Thr Phe Pro Glu Asn Glu Val Arg Lys Gly Gln Leu Gln Met
305                 310                 315                 320

Ile Glu Lys Arg Val Leu Glu Lys Lys Thr Lys Leu Gln Trp Gly Thr
                325                 330                 335

Pro Ile Ala Asp Leu Pro Ile Leu Ser Phe Glu Asp Tyr Gln His Ala
```

-continued

```
            340                 345                 350

Cys Lys Asn Asp Asn Lys Lys Trp Ile Leu Leu Glu Gly Val Val Tyr
        355                 360                 365

Asp Val Ala Asp Phe Met Ser Glu His Pro Gly Gly Glu Lys Tyr Ile
    370                 375                 380

Lys Met Gly Val Gly Lys Asp Met Thr Ala Ala Phe Asn Gly Gly Met
385                 390                 395                 400

Tyr Asp His Ser Asn Ala Ala Arg Asn Leu Leu Ser Leu Met Arg Val
                405                 410                 415

Ala Val Val Glu Tyr Gly Gly Glu Val Glu Ala Gln Lys Lys Asn Pro
            420                 425                 430

Ser Met Pro Ile Tyr Gly Thr Asp His Ala Lys Ala Glu
        435                 440                 445


<210> SEQ ID NO 5
<211> LENGTH: 3511
<212> TYPE: DNA
<213> ORGANISM: Mortierella alpina

<400> SEQUENCE: 5

ccgacacatc cacaagctgc gcatgtggcc attgcaggat gtgattcatg aaaaatacct     60

gatgcctcgg gcggacgccg actttttggc ggactttctt ggacgaatgc tgttactgga    120

tccccagttg cgcgcatctg cacaggaaat gtcccagcat ccttggctgt ttgtgaagga    180

tcctgtggac gaggaaggcg gcgagagaga cgacttccag atcagcatgg cgacaaaggg    240

agagggagac cgcgagcatg caggaaaaag tccttccggt gggcgtgaat caaaggcgac    300

tgaggacgag gaggcgaact tgtcagatca cgtcatggat gaaggcgaga actgagggtt    360

ctcacattga atttgtagcg aataaaacga cttcagaccg ttattgtcac aatcgcagga    420

tgccgatgcg aaacgaaagt ataaactggg atggtgtccg agaccgagtt ggtcaccaag    480

aggcgtccat atccggacta ccctcttttg tcagataaaa aaaaaatatc cacccaaagc    540

tggtctgtgc ttcaaaaatt tcaattatca atcatttttg attcaaaaaa aaattattca    600

gcggtattcc agtgccccaa aaaaaattgc tcacccaaat tttcttcagg cacgaaggcc    660

tgtgcgacag gtggataacc acattactct tgacaaagca catatccgtg tccgaagatc    720

gctgtgcgcg cccgcccccct gccaagtgtt cgatggcacc tgtttatcgc cgtgtcaccc    780

atccaccgaa tcaccgagtc cgactgtgtc caactgtgct ctagcgcctc acccaccagg    840

gtgtcagatg gacagcggag atgtacacgc cagtctccac atctttcggt gcacttcatc    900

cccgactacg gatcaaagct ctgctgttct gtgcagtatg tgctctccgt agcttcctag    960

agcgtggccg acaatcaact gatgctaatc gagtagttgt gaatagcatc ggacgtccat   1020

agcgataccg agtgaatgca aggcttcacc cacgactacc aagctgtgca accatgcttg   1080

cgaaagcgtt gaattattga caaaccataa caactttacg gctttgtggg agcaaggtag   1140

tcatagcgag accgaacgag ctgaggctca gtgcgcgtga aagaatgatc ttggctgcaa   1200

agaagattga taggcagcat tgagttcagt tgcactgtcg tcacagacaa ttatcctaaa   1260

ctgctttttt gactaaagag gcaattatgc tgagcaagca tgaacaaatg gacatgtcaa   1320

agggtccttg gaatagcata tttgagcaag agtgagttga ctatgagcgc accagtctag   1380

cattagcggc acgagcaaca cttggcaaga acacaccccg gctcttgcag tgttgtgcat   1440

ttggtcagtc aattttcttg ggcgtttgcg ttgcctaagt gcctatctgg agtagctttg   1500

taagatggga cttggccttt catttttttt actttagttt tttatggggc gctttttttcg   1560
```

-continued

```
ccgtcaagta tataaacccg aaggcaccgg actttctgct cctttctttc accaccatct   1620

caccttcgcc tcccgctttt ggtaccacct ctttcgcact cttgttcgat agctcgtacc   1680

ttttactctt catccttggt ggaacactgc tgccgaagca actcctcctt tcacaccctc   1740

gacctcaaac aactcgcact ccggatcgaa gagtgcagca acgcaggacg cacagcgatg   1800

gcaactcctc tccccccctc cttcgtcgtc cccgcgacac agacggaaac ccgcagagat   1860

cctctccagc acgaggaact gccccctctc ttccccgaga aaatcaccat ttacaacatc   1920

tggagatatc ttgactacaa gcatgttgtt ggtctgggac tgacaccttt gatcgcactc   1980

tacggccttt tgacgaccga gatccagacg aagaccctga tctggtccat catctactac   2040

tacgctacgg gccttggtat cacagcaggc aagttcttag tgtcccaccg gctcttttaa   2100

tataaatcac cgatttcaga atgttggggt ctgagctttt atatcgtaat acgcttttgc   2160

ggcacttgaa ttgttcgcta acattgaacc ccccacaaat ttctaattct cgtcaatgca   2220

ggttatcatc gactctgggc ccatcgtgcc tacaacgcag gacctgccat gagcttcgta   2280

ctcgcactgc ttggcgctgg tgctgttgaa ggatctatca agtggtggtc ccgcggccac   2340

cgtgctcacc accgttggac agacaccgag aaggatccct atagcgctca ccgcggactt   2400

tttttctcgc acattggctg gatgctgatc aagcgtcctg gatggaagat tggccatgcc   2460

gatgtcgacg acctcaacaa gagcaaactc gttcagtggc agcacaagaa ctacctccct   2520

cttgttctta ttatgggtgt tgtcttcccc acacttgttg ctggtctcgg ctggggcgac   2580

tggcgcggag gttacttcta tgctgccatt cttcgtcttg tctttgtcca ccacgccacc   2640

ttttgtgtca actccctggc tcactggctc ggcgatggac cctttgatga ccgccactcc   2700

ccccgcgacc actttatcac tgcctttgtc actttgggcg aaggttacca caacttccat   2760

caccagttcc cccaggacta ccgcaacgct atccgtttct accagtacga ccctacaaag   2820

tgggtcattg ccctctgcgc tttctttggc ctcgcttctc acctcaagac cttccctgag   2880

aatgaagttc gcaagggtca gctccagatg attgagaagc gtgtcttgga gaagaagacc   2940

aagcttcagt ggggcacccc cattgccgat ctgcccattc tgagctttga ggactaccag   3000

catgcctgca agaacgacaa caagaagtgg attctattgg agggcgtcgt ctacgatgtt   3060

gctgacttca tgtcagagca ccctggaggt gagaagtaca tcaagatggg cgttggcaag   3120

gacatgactg cagccttcaa cggcggcatg tacgatcaca gcaacgccgc ccgcaacttg   3180

ctgagcttga tgcgcgttgc cgtcgttgag tatggtggtg aagttgaggc tcagaagaag   3240

aacccttcga tgcccatcta cggcactgac cacgccaagg ccgaatagac ggcgagctgg   3300

cctggcccct tgtgcgcatt acaccactat acctccaccc tctcttttga gtattctttg   3360

ttagtcctac atttcacatc gactcccttg cagctattca tgaacacata gctcactcct   3420

tgtaccattt ccaacctccc tgcatcctgt aataaacact cgttctacaa ccatgtgacc   3480

taaaatgact gtagacataa aggacctgaa g                                  3511
```

<210> SEQ ID NO 6
<211> LENGTH: 27
<212> TYPE: DNA
<213> ORGANISM: Mortierella alpina

<400> SEQUENCE: 6

```
caggaattcc cgccatggca actcctc                                         27
```

<210> SEQ ID NO 7

-continued

```
<211> LENGTH: 27
<212> TYPE: DNA
<213> ORGANISM: Mortierella alpina

<400> SEQUENCE: 7

gccagcccgg gtcgccgtct attcggc                                          27


<210> SEQ ID NO 8
<211> LENGTH: 9
<212> TYPE: PRT
<213> ORGANISM: Mortierella alpina
<220> FEATURE:
<221> NAME/KEY: PEPTIDE
<222> LOCATION: Xaa is at amino acid position (5)
<223> OTHER INFORMATION: Peptide sequence derived from PCR DNA primer of
      SEQ ID No. 1; Xaa is Ala or Tyr

<400> SEQUENCE: 8

Ile Thr Ala Gly Xaa His Arg Leu Trp
  1               5


<210> SEQ ID NO 9
<211> LENGTH: 9
<212> TYPE: PRT
<213> ORGANISM: Mortierella alpina
<220> FEATURE:
<221> NAME/KEY: PEPTIDE
<222> LOCATION: Xaa is at amino acid positions (3) and (6)
<223> OTHER INFORMATION: Peptide sequence derived from PCR DNA primer of
      SEQ ID No. 2; Xaa is Phe or Tyr

<400> SEQUENCE: 9

His His Xaa Asn His Xaa Gly Glu Gly
  1               5
```